US012633390B2

(12) United States Patent
Takatori et al.

(10) Patent No.: US 12,633,390 B2
(45) Date of Patent: May 19, 2026

(54) PHYSIOLOGICAL INFORMATION PROCESSING APPARATUS, PHYSIOLOGICAL INFORMATION PROCESSING METHOD, PROGRAM AND STORAGE MEDIUM

(71) Applicant: NIHON KOHDEN CORPORATION, Tokyo (JP)

(72) Inventors: Fumihiko Takatori, Tokorozawa (JP); Masashi Sato, Tokorozawa (JP); Masayuki Inoue, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1023 days.

(21) Appl. No.: 17/753,987

(22) PCT Filed: Sep. 30, 2020

(86) PCT No.: PCT/JP2020/037341
§ 371 (c)(1),
(2) Date: Mar. 21, 2022

(87) PCT Pub. No.: WO2021/070718
PCT Pub. Date: Apr. 15, 2021

(65) Prior Publication Data
US 2023/0335252 A1     Oct. 19, 2023

(30) Foreign Application Priority Data
Oct. 11, 2019    (JP) ................................. 2019-187881

(51) Int. Cl.
*G06F 3/048*        (2013.01)
*A61M 16/00*        (2006.01)
        (Continued)

(52) U.S. Cl.
CPC ........ *G16H 20/40* (2018.01); *A61M 16/0003* (2014.02); *G16H 40/67* (2018.01);
        (Continued)

(58) Field of Classification Search
CPC .... G16H 20/40; G16H 40/67; A61M 16/0003
See application file for complete search history.

(56) References Cited

U.S. PATENT DOCUMENTS

| 7,778,691 B2* | 8/2010 | Zhang | .................. A61B 5/1135 |
| | | | 600/429 |
| 7,806,118 B2* | 10/2010 | Thompson | ........... A61H 31/008 |
| | | | 128/203.29 |

(Continued)

FOREIGN PATENT DOCUMENTS

| JP | 2003-102692 A | 4/2003 |
| JP | 2008-200111 A | 9/2008 |

(Continued)

OTHER PUBLICATIONS

Japanese Office Action dated Oct. 17, 2023 issued in Japanese Patent Application No. 2019-187881.

(Continued)

*Primary Examiner* — David Phantana-angkool
(74) *Attorney, Agent, or Firm* — McDonald Hopkins LLC

(57)        ABSTRACT

A physiological information processing apparatus comprising: a processor; and a memory that stores a computer-readable instruction that when executed by the processor, causes the physiological information processing apparatus to perform operations comprising: displaying on a display unit, first attachment position information representing a position where a first physiological information sensor is attached; acquiring first physiological information data of a subject from the first physiological information sensor; and displaying, on the display unit, information relevant to the (Continued)

first physiological information data. The physiological information processing apparatus displays the first attachment position information on the display unit before displaying the information relevant to the first physiological information data on the display unit.

10 Claims, 11 Drawing Sheets

(51) Int. Cl.
  G16H 20/40        (2018.01)
  G16H 40/67        (2018.01)

(52) U.S. Cl.
  CPC . *A61M 2205/502* (2013.01); *A61M 2205/583* (2013.01); *A61M 2230/205* (2013.01); *A61M 2240/00* (2013.01)

(56)                    References Cited

U.S. PATENT DOCUMENTS

| | | | | |
|---|---|---|---|---|
| 10,185,810 | B2 * | 1/2019 | Pathangay | ............. G16H 20/10 |
| 10,905,327 | B2 * | 2/2021 | Whiting | ............... A61B 5/6805 |
| 11,478,655 | B2 * | 10/2022 | Beattie, Jr. | ........... A61N 1/3904 |
| 11,865,352 | B2 * | 1/2024 | Alvarez | ................. G16H 40/40 |
| 12,208,273 | B2 * | 1/2025 | Elghazzawi | ......... A61N 1/3904 |
| 12,214,130 | B2 * | 2/2025 | Silver | ............... A61M 16/0003 |
| 2009/0292552 | A1 * | 11/2009 | Chen | ...................... G16H 40/67 |
| | | | | 705/2 |
| 2013/0131465 | A1 | 5/2013 | Yamamoto et al. | |
| 2016/0206839 | A1 * | 7/2016 | Freeman | ........... A61M 16/0084 |
| 2017/0277962 | A1 | 9/2017 | Kudo | |
| 2022/0096852 | A1 * | 3/2022 | Alvarez | ................. G16H 40/40 |
| 2024/0136041 | A1 * | 4/2024 | Rosenberg | ............. G16H 20/30 |
| 2025/0090852 | A1 * | 3/2025 | Dascoli | .............. A61N 1/39044 |

FOREIGN PATENT DOCUMENTS

| | | |
|---|---|---|
| JP | 2012-024390 A | 2/2012 |
| JP | 2017-169768 A | 9/2017 |
| WO | 2012-162048 A1 | 11/2012 |

OTHER PUBLICATIONS

International Search Report dated Jan. 18, 2021 issued in Patent Application No. PCT/JP2020/037341.

Written Opinion dated Jan. 18, 2021 issued in Patent Application No. PCT/JP2020/037341.

* cited by examiner

FIG. 1

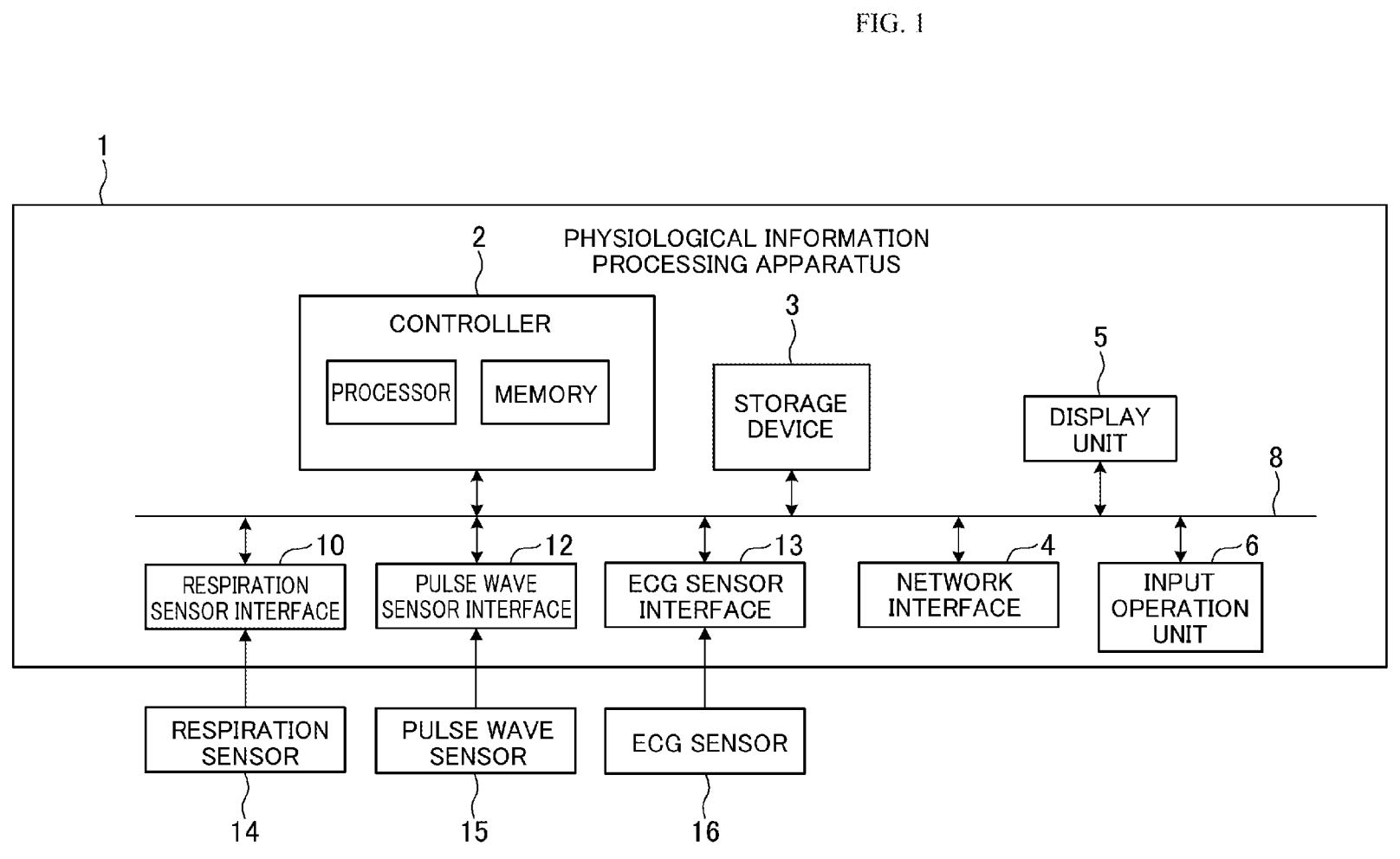

PHYSIOLOGICAL INFORMATION
PROCESSING APPARATUS

CONTROLLER

PROCESSOR

MEMORY

STORAGE
DEVICE

DISPLAY
UNIT

INPUT
OPERATION
UNIT

NETWORK
INTERFACE

ECG SENSOR
INTERFACE

ECG SENSOR

PULSE WAVE
SENSOR INTERFACE

PULSE WAVE
SENSOR

RESPIRATION
SENSOR INTERFACE

RESPIRATION
SENSOR

FIG. 10

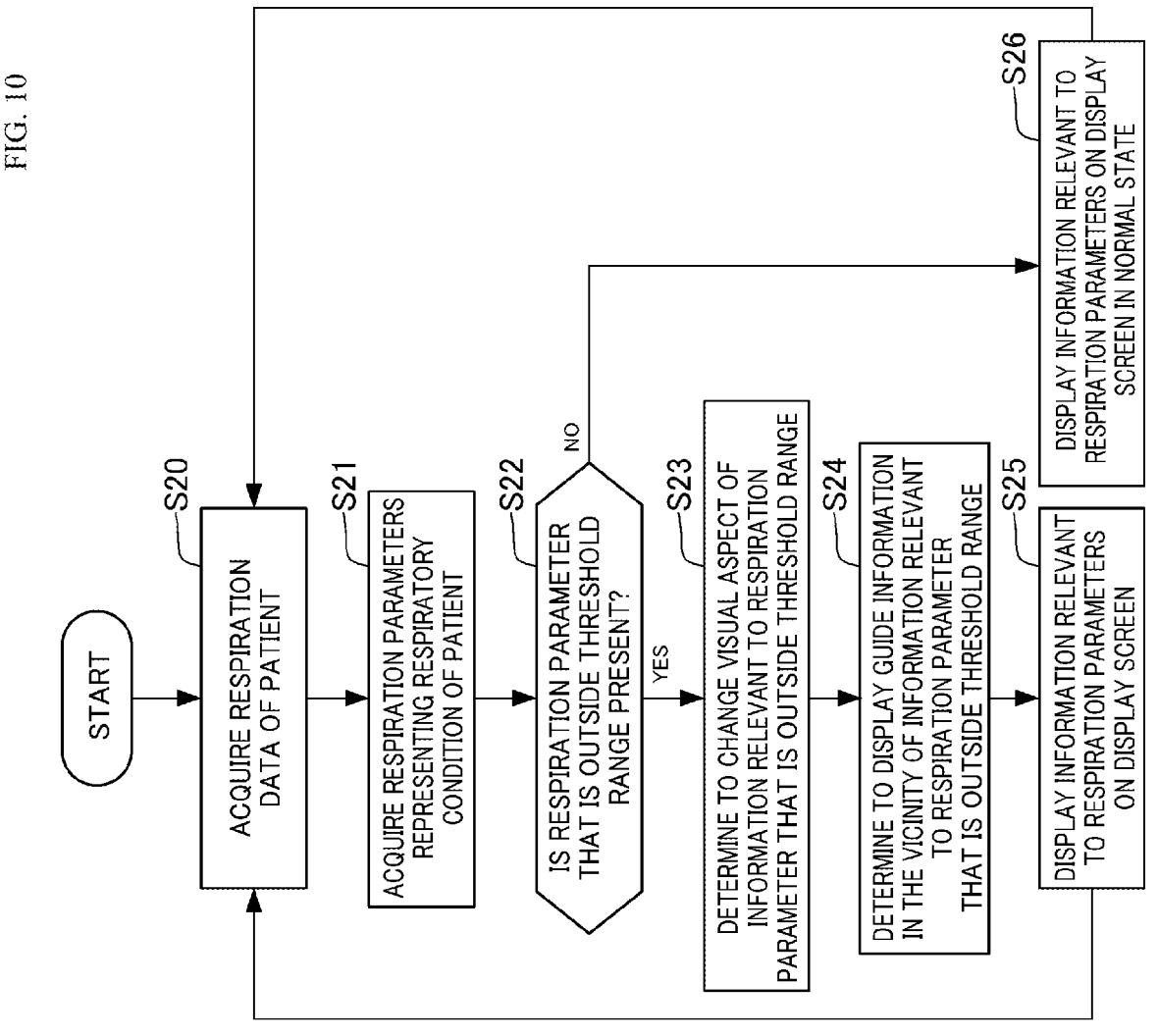

START

S20 ACQUIRE RESPIRATION DATA OF PATIENT

S21 ACQUIRE RESPIRATION PARAMETERS REPRESENTING RESPIRATORY CONDITION OF PATIENT

S22 IS RESPIRATION PARAMETER THAT IS OUTSIDE THRESHOLD RANGE PRESENT?

NO

YES

S23 DETERMINE TO CHANGE VISUAL ASPECT OF INFORMATION RELEVANT TO RESPIRATION PARAMETER THAT IS OUTSIDE THRESHOLD RANGE

S24 DETERMINE TO DISPLAY GUIDE INFORMATION IN THE VICINITY OF INFORMATION RELEVANT TO RESPIRATION PARAMETER THAT IS OUTSIDE THRESHOLD RANGE

S25 DISPLAY INFORMATION RELEVANT TO RESPIRATION PARAMETERS ON DISPLAY SCREEN

S26 DISPLAY INFORMATION RELEVANT TO RESPIRATION PARAMETERS ON DISPLAY SCREEN IN NORMAL STATE

PHYSIOLOGICAL INFORMATION PROCESSING APPARATUS, PHYSIOLOGICAL INFORMATION PROCESSING METHOD, PROGRAM AND STORAGE MEDIUM

TECHNICAL FIELD

The present disclosure relates to a physiological information processing apparatus, a physiological information processing method, a program and a storage medium.

BACKGROUND ART

In order to grasp a health condition of a patient, a bedside monitor which can simultaneously display a plurality of pieces of physiological information of the patient on a display screen is being used at a current medical site. A physiological information monitor apparatus to which physiological information sensors such as an electrocardiogram (ECG) sensor and a respiration sensor are connected has been disclosed in JP-A-2008-200111.

In order to accurately grasp vital signs of a patient by use of the physiological information monitor apparatus, the physiological information sensors for detecting physiological information data of the patient are required to be attached to the patient appropriately. In this respect, when positions where the physiological information sensors are attached are wrong, a medical worker such as a doctor cannot grasp the vital signs of the patient accurately. Particularly when the medical worker is not familiar with attachment of the physiological information sensors to the patient, a situation that the physiological information sensors are attached at wrong positions can be anticipated. Thus, there is still room for further consideration about measures which can be taken in order to prevent such a situation.

SUMMARY

The present disclosure is directed to improving the usability of a physiological information processing apparatus from the aforementioned viewpoint. Particularly, the present disclosure is directed to providing a physiological information processing apparatus through which a medical worker can attach a physiological information sensor at an appropriate position, a physiological information processing method, a program and a storage medium.

According to one or more aspects of the present disclosure, there is provided a physiological information processing apparatus.

The physiological information processing apparatus comprises:

a processor; and a memory that stores a computer-readable instruction that when executed by the processor, causes the physiological information processing apparatus to perform operations comprising:

displaying on a display unit, first attachment position information representing a position where a first physiological information sensor is attached;

acquiring first physiological information data of a subject from the first physiological information sensor; and displaying, on the display unit, information relevant to the first physiological information data.

The physiological information processing apparatus displays the first attachment position information on the display unit before displaying the information relevant to the first physiological information data on the display unit.

According to one or more aspects of the present disclosure, there is provided a physiological information processing apparatus.

The physiological information processing apparatus comprises:

a processor; and a memory that stores a computer-readable instruction that when executed by the processor, causes the physiological information processing apparatus to perform operations comprising:

acquiring a parameter representing a physiological condition of a subject;

displaying information relevant to the parameter on a display unit;

determining whether or not the acquired parameter is included in a threshold range; and displaying, on the display unit, guide information guiding a user to perform an operation such that the parameter is included in the threshold range, when the parameter is outside the threshold range.

According to one or more aspects of the present disclosure, there is provided a physiological information processing method executed by a computer.

The method comprises:

displaying, on a display unit, first attachment position information representing a position where a first physiological information sensor is attached;

acquiring first physiological information data of a subject from the first physiological information sensor; and displaying, on the display unit, information relevant to the first physiological information data.

The first attachment position information is displayed on the display unit before the information relevant to the first physiological information data is displayed on the display unit.

According to one or more aspects of the present disclosure, there is provided a physiological information processing method executed by a computer.

The method comprises:

acquiring a parameter representing a physiological condition of a subject;

displaying, on a display unit, information relevant to the parameter;

determining whether or not the acquired parameter is included in a threshold range; and displaying, on the display unit, guide information guiding a user to perform an operation such that the parameter is included in the threshold range, when the parameter is outside the threshold range.

BRIEF DESCRIPTION OF DRAWINGS

FIG. 1 is a block diagram illustrating a physiological information processing apparatus.

FIG. 10 is a flow chart for describing a physiological information processing method according to a second embodiment.

DESCRIPTION OF EMBODIMENT

First Embodiment

Figure 2:
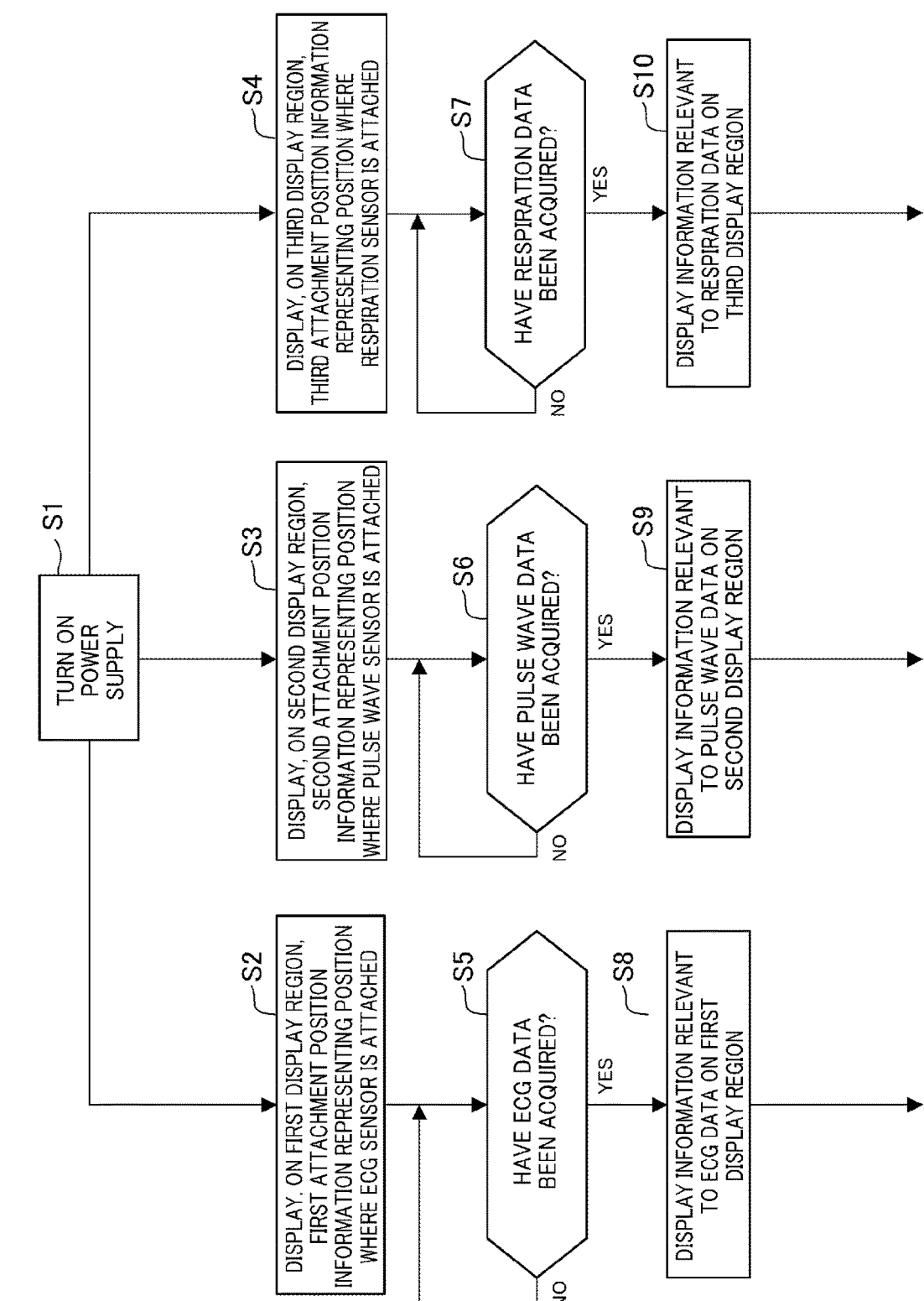
FIG. 2 is a flow chart for describing a physiological information processing method according to a first embodiment.

A physiological information processing method according to a first embodiment will be described below with reference to the drawings. In the first place, a physiological information processing apparatus 1 (which will be hereinafter referred to as "processing apparatus 1" simply) according to the first embodiment will be described below with reference to FIG. 1. FIG. 1 is a block diagram showing the processing apparatus 1.

The processing apparatus 1 may be a physiological information monitor (bedside monitor) which is configured to display physiological information of a patient (subject). In addition, the processing apparatus 1 may be a personal computer, a work station, a smartphone, a tablet, or a wearable device (such as AR glasses etc.) worn on the body (such as an arm or a portion of the head) of a medical worker.

As shown in FIG. 1, the processing apparatus 1 is connected to a respiration sensor 14, a pulse wave sensor 15, and an ECG sensor 16. The processing apparatus 1 is configured to acquire respiration data (such as airway pressure data, ventilation volume data, expired gas concentration data, etc.) of a patient as physiological information data from the respiration sensor 14. The processing apparatus 1 is configured to acquire pulse wave data of the patient as physiological information data from the pulse wave sensor 15. The processing apparatus 1 is configured to acquire ECG data of the patient as physiological information data from the ECG sensor 16.

The processing apparatus 1 includes a controller 2, a storage device 3, a network interface 4, a display unit 5, and an input operation unit 6. The processing apparatus 1 further includes a respiration sensor interface 10, a pulse wave sensor interface 12, and an ECG sensor interface 13. The respective constituent elements of the processing apparatus 1 may be communicably connected to one another through a bus 8.

The controller 2 includes a memory and a processor. The memory is configured to store a computer-readable instruction (program). For example, the memory may be constituted by an ROM (Read Only Memory) in which various programs etc. have been stored, and an RAM (Random Access Memory) or the like which has a plurality of work areas in which the various programs etc. executed by the processor can be stored. In addition, the memory may be constituted by a flash memory etc. The processor includes, for example, at least one of a CPU (Central Processing Unit), an MPU (Micro Processing Unit), and a GPU (Graphics Processing Unit). In addition, the processor may include an FPGA (Field-Programmable Gate Array) and/or an ASIC (Application Specific Integrated Circuit). The CPU may be constituted by a plurality of CPU cores. The GPU may be constituted by a plurality of GPU cores. The processor may be configured to expand, onto the RAM, a physiological information program designated from the various programs which have been incorporated into the storage device 3 or the ROM, and to execute various processes in cooperation with the RAM.

The storage device 3 is, for example, a storage device (storage) such as an HDD (Hard Disk Drive), an SSD (Solid State Drive), or a flash memory, which is configured to store the programs or various data. The physiological information processing program may be incorporated into the storage device 3.

The network interface 4 is configured to connect the processing apparatus 1 to a communication network. Specifically, the network interface 4 may include various wired connection terminals for making communication with an external server through the communication network (such as an LAN, a WAN or the Internet). In addition, the network interface 4 may include a communication processing circuit such as an RF circuit, a transmission/reception antenna, etc. for making wireless communication with an access point (such as a wireless LAN router or a wireless base station). A wireless communication standard between the access point and the processing apparatus 1 is, for example, Wi-Fi (registered trademark), Bluetooth (registered trademark), Zigbee (registered trademark), LPWA or a fifth-generation mobile communication system (5G).

The display unit 5 may be a display device such as a liquid crystal display or an organic EL display. In addition, the display unit 5 may be a display device such as a transmission type or non-transmission type head mount display or an AR display which can be worn on the head of an operator. Further, the display unit 5 may be a projector device projecting an image on a screen. In addition, the processing apparatus 1 may not include the display unit 5. In this case, an external display device may display image data transmitted from the processing apparatus 1 after the processing apparatus 1 transmits the image data to the external display device by wire or by wireless.

The input operation unit 6 is configured to accept an input operation of the medical worker operating the processing apparatus 1 and to generate an instruction signal in accordance with the input operation. The input operation unit 6 is, for example, a touch panel disposed to be superimposed on the display unit 5, a mouse, a keyboard, and/or a physical operation button etc. disposed on a housing of the processing apparatus 1. After the instruction signal generated by the input operation unit 6 is transmitted to the controller 2 through the bus 8, the controller 2 executes a predetermined operation in accordance with the instruction signal.

The respiration sensor interface 10 is an interface for connecting the respiration sensor 14 and the processing apparatus 1 to each other. The respiration sensor interface 10 may be physically connected to a cable connector of the respiration sensor 14. In addition, the respiration sensor interface 10 may have an analog processing circuit including an amplifier and an A/D converter, and a digital processing circuit including a processor such as a CPU and a memory such as an ROM. The respiration sensor interface 10 is configured to generate respiration data (digital data) based on an output result representing a respiratory condition of the patient acquired by the respiration sensor 14. The respiration data may include airway pressure data representing temporal change of airway pressure and ventilation volume data representing temporal change of a ventilation volume.

Figure 9:
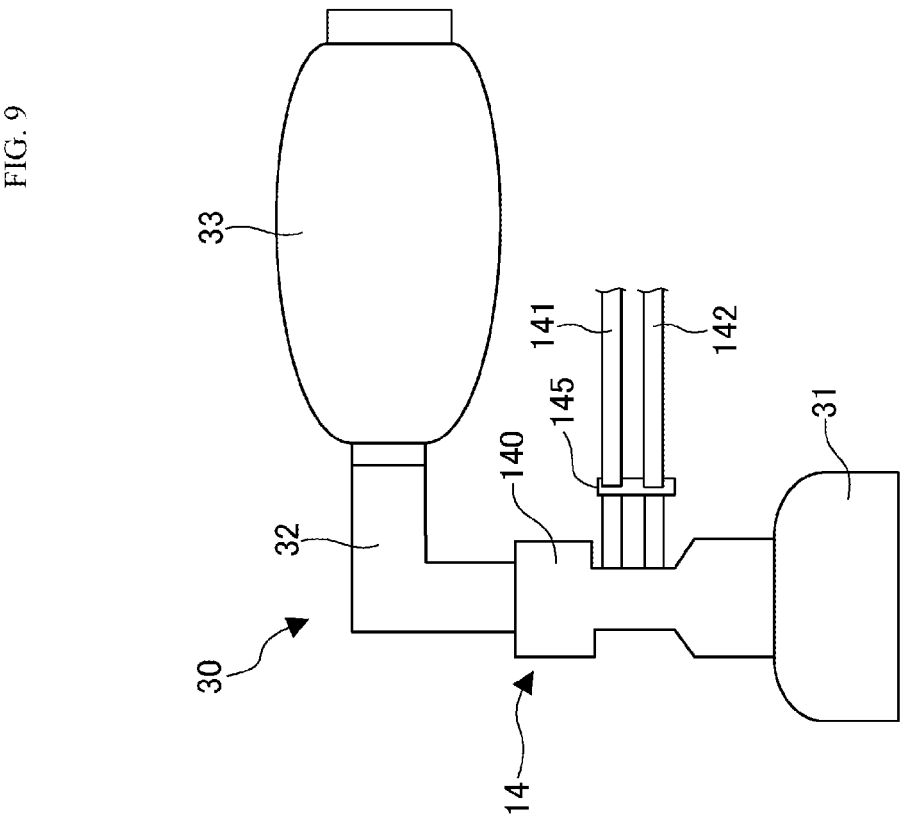
FIG. 9 is a schematic view illustrating a ventilation device and a respiration sensor attached to the ventilation device.

An example of the structure of a ventilation device 30 which is mounted on the face of the patient and the respiration sensor 14 which detects the respiratory condition of the patient will be described with reference to FIG. 9. FIG. 9 is a schematic view showing the ventilation device 30 and the respiration sensor 14 attached to the ventilation device 30. As shown in FIG. 9, the ventilation device 30 has a face mask 31, an air duct 32, and a respiration bag 33. The ventilation device 30 is a ventilation medical appliance for non-invasively performing positive pressure ventilation on the patient such as a newborn baby who does not respire spontaneously or who is low in heart rate. The medical worker (user) can perform positive pressure ventilation on the patient manually or automatically (semi-automatically) by use of the ventilation device 30.

The face mask 31 is configured to cover the mouth and the nose of the patient (such as the newborn baby). The air duct 32 is configured to allow air supplied from the respiration bag 36 to pass through. A backflow valve or a bacterial filter may be provided in the air duct 32. The respiration bag 33 communicating with the air duct 32 is configured to supply air to the patient in accordance with an operation of the medical worker. In this respect, the medical worker squeezes the respiration bag 33 with his/her hands so that air is supplied to the patient through the air duct 32, a measurement tube 140 and the face mask 31.

Next, the respiration sensor 14 will be described. The respiration sensor 14 is configured to detect the respiratory condition of the patient (subject) to whom the ventilation device 30 has been attached. Particularly, the respiration sensor 14 is configured to detect airway pressure and a ventilation volume of the patient.

The respiration sensor 14 may be, for example, a flow sensor. As an example of the configuration of the respiration sensor 14, the respiration sensor 14 has the measurement tube 140 (an example of a columnar body) connected to the face mask 31 and the air duct 32, an inspiration side air tube 141, an expiration side air tube 142, and a connection portion 145 connecting the inspiration side air tube 141 and the expiration side air tube 142 with the measurement pipe 140.

The measurement tube 140 which is configured as a circularly columnar tube communicates with the air duct 32 and the face mask 31. A variable orifice moving according to an inspiration side (respiration bag 33 side) flow or an expiration side (face mask 31 side) flow may be provided inside the measurement tube 140.

The inspiration side air tube 141 is configured to transmit flow and pressure of inspiration side air of the measurement tube 140. The expiration side air tube 142 is configured to transmit flow and pressure of expiration side air of the measurement tube 140. In addition, a differential pressure sensor is provided in one of the respiration sensor 14 and the respiration sensor interface 10. The differential pressure sensor is configured to detect differential pressure between the pressure of the inspiration side air and the pressure of the expiration side air.

The analog processing circuit of the respiration sensor interface 10 may convert, into digital data, differential pressure data representing the differential pressure between the pressure of the inspiration side air and the pressure of the expiration side air, which has been acquired by the differential pressure sensor. Then, the digital processing circuit of the respiration sensor interface 10 may acquire respiration data (airway pressure data and ventilation volume data) based on the differential pressure data (the digital data).

Return to FIG. 1. The pulse wave sensor interface 12 is an interface for connecting the pulse wave sensor 15 and the processing apparatus 1 to each other. The pulse wave sensor 15 which is, for example, a pulse oximeter probe is configured to be worn on a finger of the patient. The pulse wave sensor 15 is provided with a light emitter and a light receiver. The light emitter is configured to radiate light toward the finger of the patient. The light emitter is, for example, an LED (Light Emitting Diode). The light emitter has a red light LED configured to emit a red light beam, and an infrared light LED configured to emit an infrared light beam. The red light LED and the infrared light LED are driven and controlled to emit the light beams alternately.

The light receiver is configured to generate a physiological signal (electrical signal) upon reception of light, which has been radiated from the light emitter and passed through the finger of the patient. The light receiver is, for example, a photoelectric conversion element such as a PD (photodiode). The number of the light receivers is not limited particularly. When, for example, the light emitter has the red light LED and the infrared light LED, the light receiver has photosensitivity to the red light radiated from the red light LED and the infrared light radiated from the infrared light LED.

The pulse wave sensor interface 12 may be physically connected to a cable connector of the pulse wave sensor 15. In addition, the pulse wave sensor interface 12 may have an analog processing circuit which includes an amplifier and an A/D converter. The pulse wave sensor interface 12 is configured to generate pulse wave data (digital data) based on the physiological signal which has been acquired by the pulse wave sensor 15. The pulse wave data have information about intensity of light received by the light receiver of the pulse wave sensor 15, and time information. The pulse wave data may include pulse wave data associated with the red light, and pulse wave data associated with the infrared light.

The ECG sensor interface 13 is an interface for connecting the ECG sensor 16 and the processing apparatus 1 to each other. The ECG sensor 16 has, for example, a plurality of electrodes (e.g. three electrodes) which are attached to a chest portion of the patient. The ECG sensor 16 is configured to contact a measurement portion of the patient and detect potential change of the measurement portion.

The ECG sensor interface 13 may be physically connected to a cable connector of the ECG sensor 16. The ECG sensor interface 13 may have an analog processing circuit including a differential amplifier and an A/D converter. The differential amplifier is configured to differentially amplify a potential outputted from one measurement electrode of the ECG sensor 16 and a potential outputted from another measurement electrode of the ECG sensor 16 to thereby generate ECG data (analog data). The A/D converter is configured to convert the ECG data (the analog data) into digital data. Thus, the ECG data (the digital data) are generated by the ECG sensor interface 13.

Next, the physiological information processing method according to the first embodiment will be described below with reference to FIG. 2 to FIG. 6. FIG. 2 is a flow chart for describing the physiological information processing method according to the first embodiment. As shown in FIG. 2, a power supply of the processing apparatus 1 is turned ON by a medical worker (user) in a step S1.

Next, in a step S2, the controller 2 of the processing apparatus 1 shown in FIG. 1 displays, on the display unit 5, first attachment position information representing an attachment position of the ECG sensor 16 (an example of a first physiological information sensor) to a patient. Specifically, the controller 2 displays the first attachment position information on a first display region G1 of a display screen 20 (GUI screen) of the display unit 5 (see FIG. 3). The first attachment position information is displayed as illustration information on the first display region G1.

Next, in a step S3, the controller 2 displays, on the display unit 5, second attachment position information representing an attachment position of the pulse wave sensor 15 (an example of a second physiological information sensor) to the patient. Specifically, the controller 2 displays the second attachment position information on a second display region G2 of the display screen 20 (see FIG. 3). The second attachment position information is also displayed as illustration information on the second display region G2.

Next, in a step S4, the controller 2 displays, on the display unit 5, third attachment position information representing an attachment position of the respiration sensor 14 (an example of a third physiological information sensor) to the patient. Specifically, the controller 2 displays the third attachment position information on a third display region G3 of the display screen 20 (see FIG. 3). The third attachment position information is also displayed as illustration information on the third display region G3.

Figure 3:
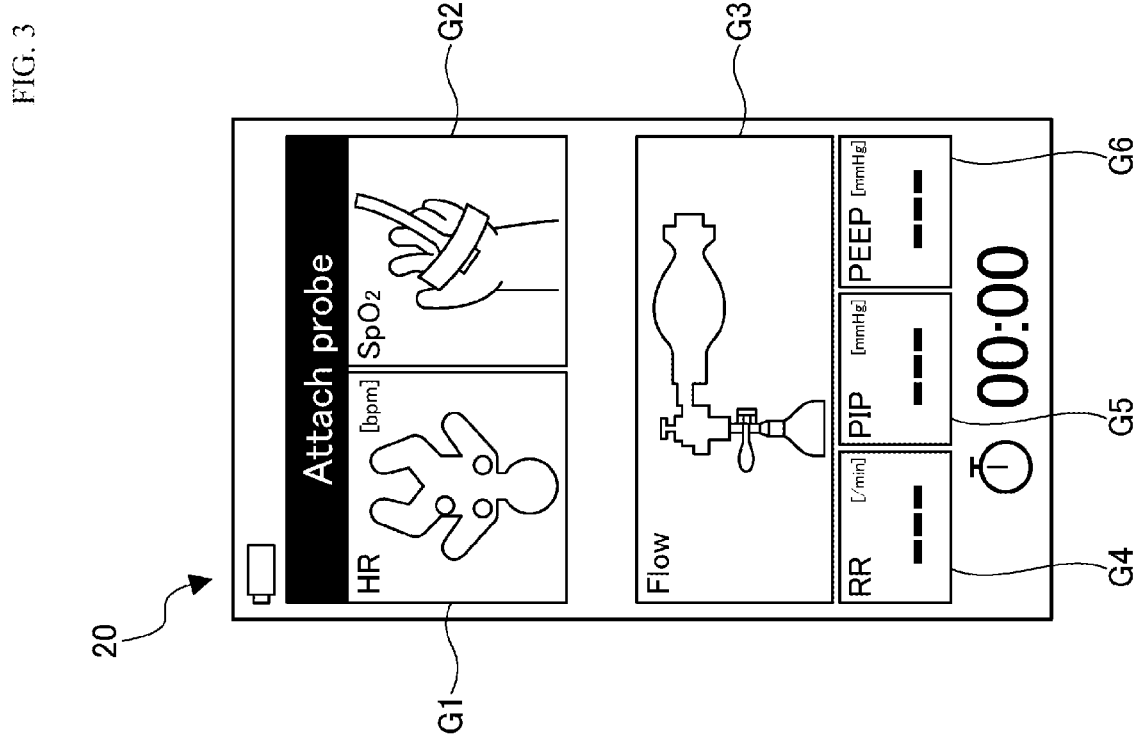
FIG. 3 is a view illustrating an example of a display screen on which first attachment position information, second attachment position information and third attachment position information are displayed.

In this manner, the controller 2 simultaneously displays the first attachment position information, the second attachment position information and the third attachment position information on the display screen 20 of the display unit 5, as shown in FIG. 3.

Next, in a step S5, the controller 2 determines whether ECG data (an example of first physiological information data) of the patient have been acquired or not from the ECG sensor 16 through the ECG sensor interface 13. When the determination result of the step S5 is YES, the controller 2 executes processing of a step S8. On the other hand, when the determination result of the step S5 is NO, the determination processing of the step S5 is executed repeatedly.

In addition, in a step S6, the controller 2 determines whether pulse wave data (an example of second physiological information data) of the patient have been acquired or not from the pulse wave sensor 15 through the pulse wave sensor interface 12. When the determination result of the step S6 is YES, the controller 2 executes processing of a step S9. On the other hand, when the determination result of the step S6 is NO, the determination processing of the step S6 is executed repeatedly.

Further, in a step S7, the controller 2 determines whether respiration data (an example of third physiological information data) of the patient have been acquired or not from the respiration sensor 7 through the respiration sensor interface 10. When the determination result of the step S7 is YES, the controller 2 executes processing of a step S10. On the other hand, when the determination result of the step S7 is NO, the determination processing of the step S7 is executed repeatedly.

Figure 4:
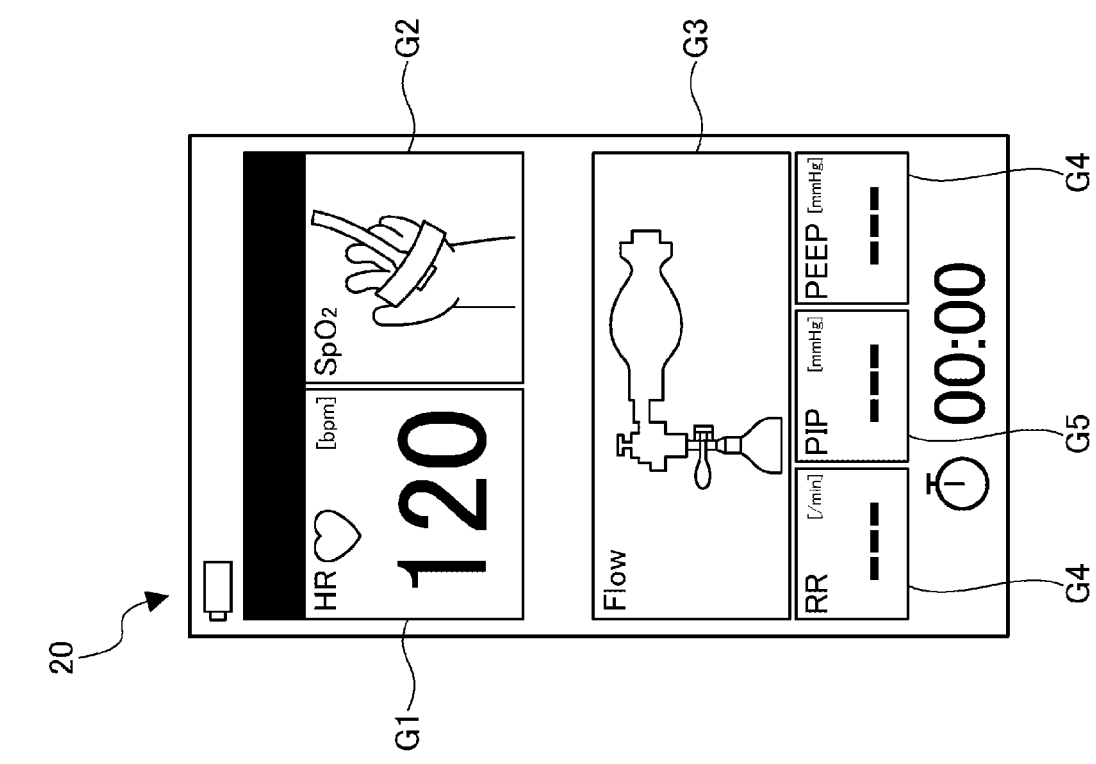
FIG. 4 is a view illustrating an example of a display screen on which information relevant to ECG data, the second attachment position information and the third attachment position information are displayed.

Next, in the step S8, the controller 2 displays information relevant to the ECG data on the first display region G1 (see FIG. 4). Specifically, after having identified a heart rate (times/minute) of the patient based on the ECG data, the controller 2 displays a value of the identified heart rate (an example of the information relevant to the ECG data) on the first display region G1. Thus, in the case where the ECG data have been acquired, the controller 2 changes the information displayed on the first display region G1 of the display screen 20 to the value of the heart rate.

Figure 5:
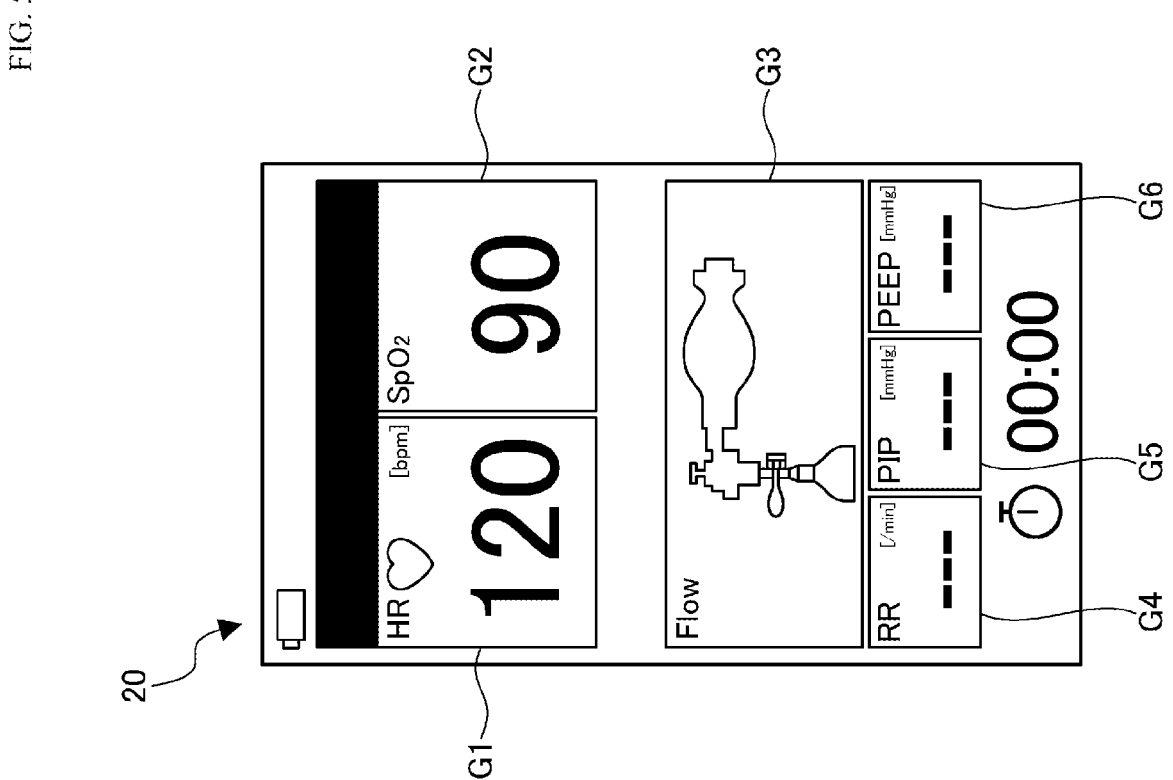
FIG. 5 is a view illustrating an example of the display screen on which the information relevant to the ECG data, information relevant to pulse wave data and the third attachment position information are displayed.
Figure 6:
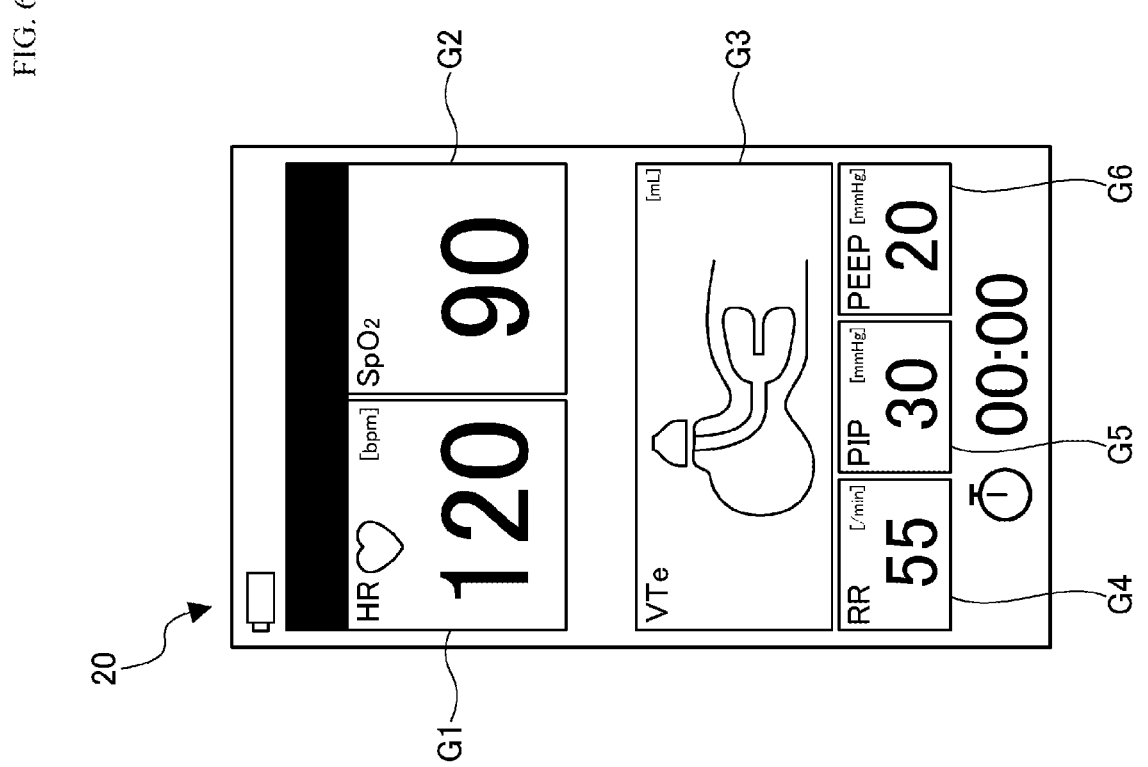
FIG. 6 is a view illustrating an example of the display screen on which the information relevant to the ECG data, the information relevant to the pulse wave data and information relevant to respiration data are displayed.

In addition, in the step S9, the controller 2 displays information relevant to the pulse wave data on the second display region G2 (see FIG. 5). Specifically, after having identified arterial oxygen saturation (SpO2(%)) of the patient based on pulse wave data associated with red light and pulse wave data associated with infrared light, the controller 2 displays a value of the identified SpO2 (an example of the information relevant to the pulse wave data) on the second display region G2. Thus, in the case where the pulse wave data have been acquired, the controller 2 changes the information displayed on the second display region G2 of the display screen 20 from the second attachment position information to the value of the SpO2.

Next, in the step S10, the controller 2 displays information relevant to the respiration data on the third display region G3. Further, the controller 2 displays the information relevant to the respiration data on a fourth display region G4, a fifth display region G5 and a sixth display region G6 (see FIG. 6). Specifically, based on the respiration data, the controller 2 acquires parameters relevant to a ventilation volume of the patient, parameters relevant to airway pressure of the patient and a parameter relevant to a respiration rate of the patient as respiration parameters.

(Parameters Relevant to Ventilation Volume of Patient)

The controller 2 acquires the parameters relevant to the ventilation volume of the patient based on ventilation volume data which are an example of the respiration data. Particularly, the controller 2 acquires an inspired tidal volume (VTi) sent to the patient from the ventilation device 30 shown in FIG. 9 and an expired tidal volume (VTe) returned from the patient to the ventilation device 30. Further, the controller 2 calculates a leak ratio (%) of positive pressure ventilation representing a ratio of air leaking out from the face mask 31 based on the VTi and the VTe. Here, the leak ratio is calculated as $(VTi-VTe)/VTi \times 100\%$. Then, the controller 2 displays, on the third display region G3, illustration information (an example of information relevant to the respiration data) representing a degree of the leak ratio of the positive pressure ventilation.

(Parameters Relevant to Airway Pressure of Patient)

In addition, the controller 2 identifies the parameters relevant to the airway pressure of the patient based on airway pressure data which are an example of the respiration data. Particularly, the controller 2 identifies peak inspiratory pressure (PIP) which is highest airway pressure in a respiration cycle, and positive end-expiratory pressure (PEEP). Then, the controller 2 displays a value of the PIP (an example of information relevant to the respiration data) on the fifth display region G5, and displays a value of the PEEP (an example of information relevant to the respiration data) on the sixth display region G6.

(Parameter Relevant to Respiration Rate of Patient)

In addition, the controller 2 identifies the parameter relevant to the respiration rate of the patient based on the airway pressure data. That is, the controller 2 identifies the respiration rate (RR) of the patient. Then, the controller 2 displays a value of the RR (an example of information relevant to the respiration data) on the fourth display region G4.

In this manner, the series of processes according to the physiological information processing method according to the first embodiment are executed. In addition, in accordance with an input operation performed on the processing apparatus 1 by the medical worker, the information displayed on the third display region G3 may be changed from the illustration information (see FIG. 6) representing the degree of the leak ratio to an airway pressure waveform (see FIG. 7) representing temporal change of the airway pressure data.

In accordance with an input operation performed on the processing apparatus 1 by the medical worker, the information displayed on the first display region G1 may be likewise changed from the value of the heart rate (see FIG. 6) to an ECG waveform representing temporal change of the ECG data or a heart rate waveform representing temporal change of the heart rate.

Further, in accordance with an input operation performed on the processing apparatus 1 by the medical worker, the information displayed on the second display region G2 may be changed from the value of the SpO2 (see FIG. 6) to a pulse wave waveform representing temporal change of the pulse wave data or an SpO2 waveform representing temporal change of the SpO2.

According to the present embodiment, the first attachment position information representing the attachment position of the ECG sensor 16 is displayed on the first display region G1 before the information relevant to the ECG data is displayed on the first display region G1. In addition, the second attachment position information representing the attachment position of the pulse wave sensor 15 is displayed on the second display region G2 before the information relevant to the pulse wave data is displayed on the second display region G2. Further, the third attachment position information representing the attachment position of the respiration sensor 14 is displayed on the third display region G3 before the information relevant to the respiration data is displayed from the third display region G3 to the sixth display region G6.

Therefore, by confirming each of the first attachment position information to the third attachment position information displayed on the display screen 20, even a medical worker who is not familiar with attachment of the ECG sensor 16, the pulse wave sensor 15 and the respiration sensor 14 can attach the ECG sensor 16, the pulse wave sensor 15 and the respiration sensor 14 at respective appropriate positions. In this manner, the usability of the processing apparatus 1 can be improved.

Further, in the case where the ECG data have been acquired, the information displayed on the first display region G1 is changed from the first attachment position information to the information relevant to the ECG data. In addition, in the case where the pulse wave data have been acquired, the information displayed on the second display region G2 is changed from the second attachment position information to the information relevant to the pulse wave data. Further, in the case where the respiration data have been acquired, the information displayed on the third display region G3 is changed from the third attachment position information to the information relevant to the respiration data. Thus, without any input operation performed on the processing apparatus 1 by the medical worker, the information displayed on the display screen 20 can be automatically changed from the attachment position information of the physiological information sensors to the information relevant to the physiological information data. Accordingly, the usability of the processing apparatus 1 can be further improved.

Figure 7:
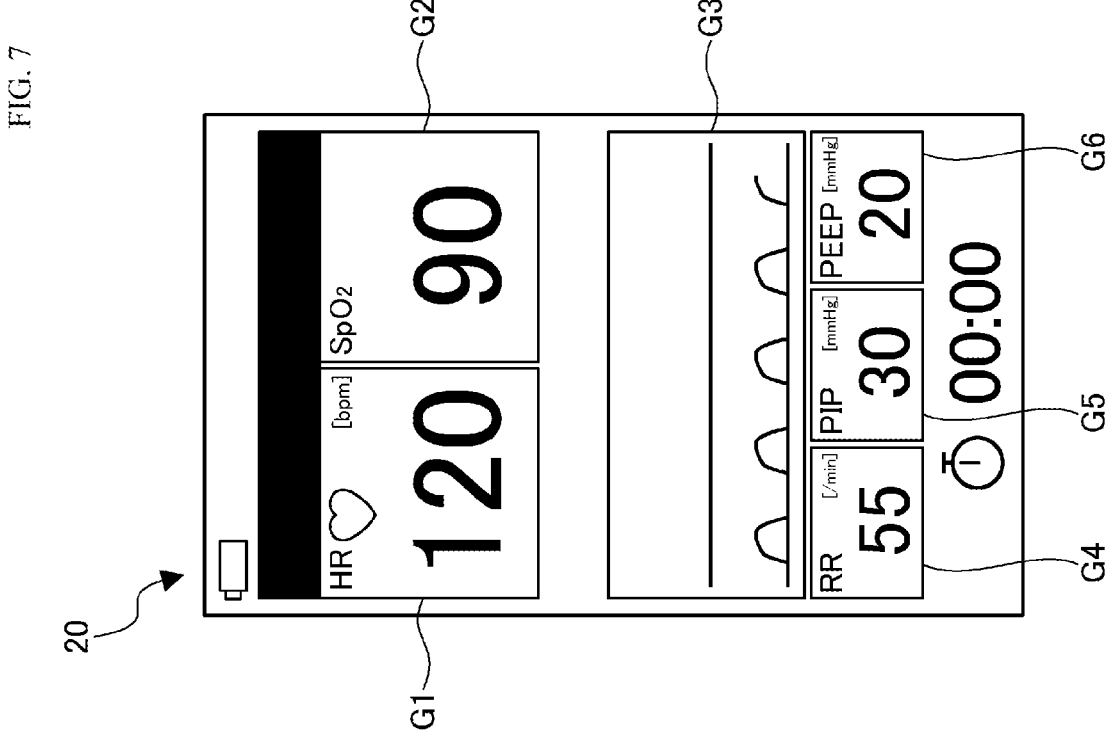
FIG. 7 is a view illustrating an example of the display screen on which a waveform representing temporal change of airway pressure data is displayed as the information relevant to the respiration data.
Figure 8:
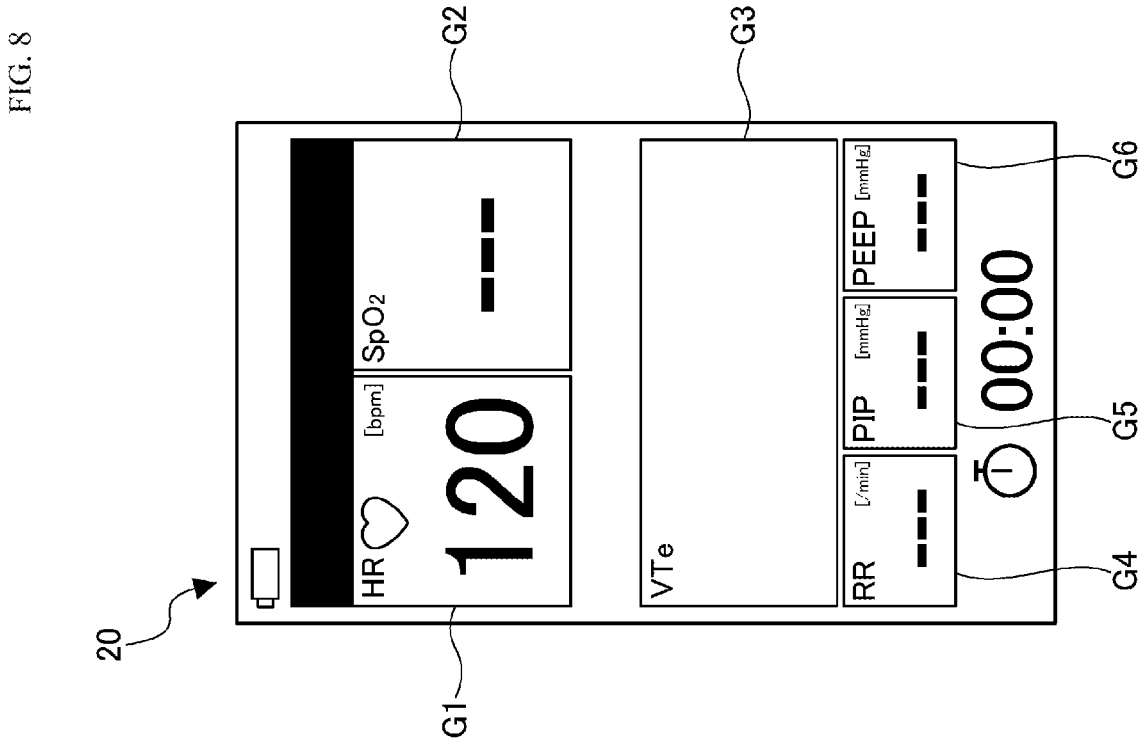
FIG. 8 is a view illustrating an example of the display screen on which only the information relevant to the ECG data is displayed.

In the present embodiment, in a case where the ECG data have been acquired but the pulse wave data and the respiration data have not been acquired, the value of the heart rate is displayed on the first display region G1 but the second attachment position information and the third attachment position information are displayed on the second display region G2 and the third display region G3 respectively, as shown in FIG. 4. However, the present embodiment is not limited to such a display method. In this respect, even in the case where the ECG data have been acquired but the pulse wave data and the respiration data have not been acquired, the second attachment position information and the third attachment position information may not be displayed on the second display region G2 and the third display region G3 respectively, as shown in FIG. 7. That is, in the case where at least one of a plurality of pieces of physiological information data has been acquired, attachment position information of the physiological information sensors may disappear from the display screen 20.

Second Embodiment

Figure 11:
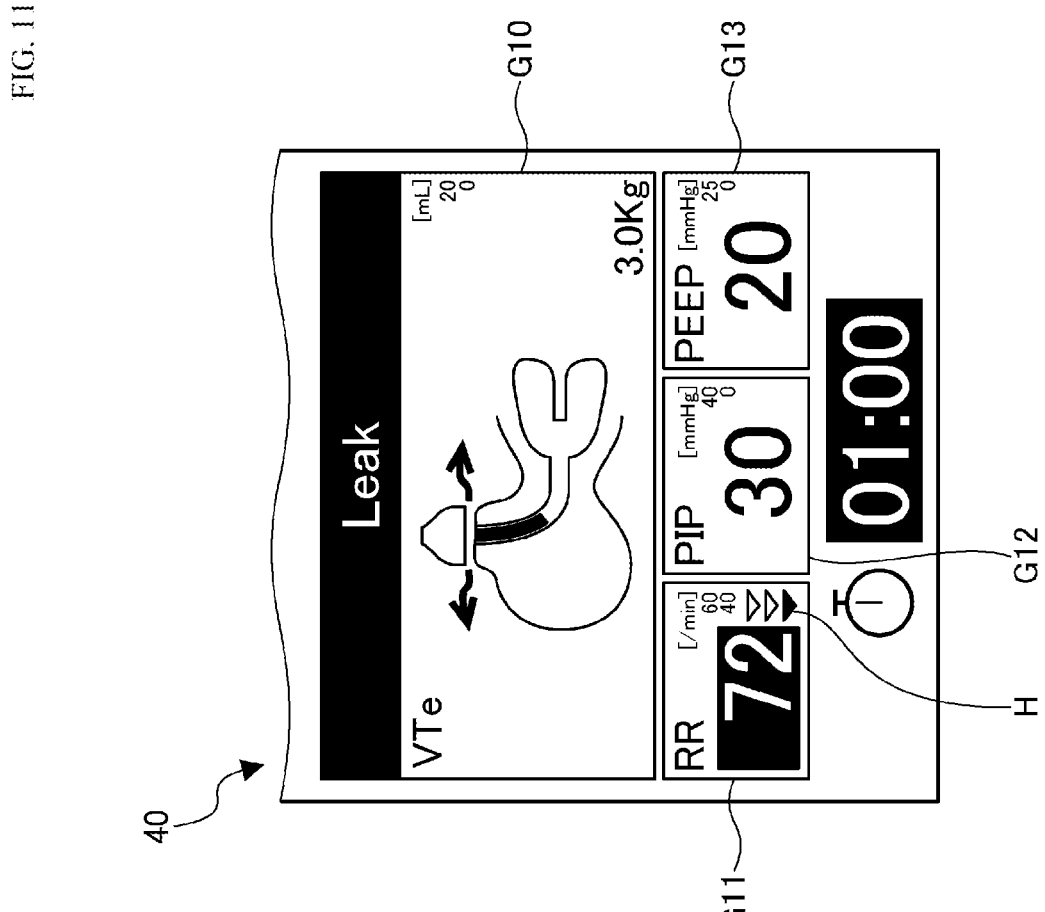
FIG. 11 is a view illustrating an example of a display screen on which information relevant to a plurality of respiration parameters and guide information are displayed.

Next, a physiological information processing method according to a second embodiment will be described below with reference to FIG. 10 and FIG. 11. FIG. 10 is a flow chart for describing the physiological information processing method according to the second embodiment. FIG. 11 is a view showing an example of a display screen 40 on which information relevant to a plurality of respiration parameters and guide information H are displayed. Incidentally, assume that the processing apparatus 1 shown in FIG. 1 executes the physiological information processing method according to the second embodiment. Therefore, the respective constituent elements (such as the controller 2 etc.) of the processing apparatus 1 shown in FIG. 1 will be mentioned suitably in the following description.

In a step S20 as shown in FIG. 10, the controller 2 acquires respiration data (ventilation volume data and airway pressure data) of a patient on whom the ventilation device 30 (see FIG. 9) has been mounted, from the respiration sensor 14 through the respiration sensor interface 10. Next, in a step S21, the controller 2 acquires respiration parameters representing a respiratory condition (an example of physiological parameters representing a physiological condition) of the patient on whom the ventilation device 30 has been mounted. Specifically, based on the respiration data, the controller 2 acquires parameters (specifically, VTi, VTe and a leak ratio of positive pressure ventilation) relevant to a ventilation volume of the patient, parameters (specifically, PIP and PEEP) relevant to airway pressure of the patient, and a respiration rate RR of the patient respectively.

Next, in a step S22, the controller 2 determines whether each of the respiration parameters of the patient is included or not in a threshold range. In this respect, the controller 2 determines whether each (e.g. the VTe or the leak ratio) of the parameters relevant to the ventilation volume of the patient is included or not in a threshold range. For example, assume that the threshold range of the VTe is set to be not lower than 0 mL and not higher than 20 mL. In this case, the controller 2 determines whether the acquired VTe is included or not in the threshold range which is not lower than 0 mL and not higher than 20 mL.

In addition, the controller 2 determines whether each of the parameters (e.g. PIP and PEEP) relevant to the airway pressure of the patient is included or not in a threshold range. For example, assume that the threshold range of the PIP is set to be not lower than 8 mmHg and not higher than 40 mmHg. In this case, the controller 2 determines whether the acquired PIP is included or not in the threshold range which is not lower than 8 mmHg and not higher than 40 mmHg. Further, assume that the threshold range of the PEEP is set to be not lower than 0 mmHg and not higher than 25 mmHg. In this case, the controller 2 determines whether the acquired PEEP is included or not in the threshold range which is not lower than 0 mmHg and not higher than 25 mmHg.

Further, the controller 2 determines whether the respiration rate RR of the patient is included or not in a threshold range. For example, assume that the threshold range of the RR is set to be not lower than 40 times/minute and not higher than 60 times/minute. In this case, the controller 2 determines whether the identified RR is included or not in the threshold range which is not lower than 40 times/minute and not higher than 60 times/minute.

Having determined in the step S22 that at least one of the respiration parameters of the patient is outside the corresponding threshold range (in other words, having determined in the step S22 that a respiration parameter which is outside the corresponding threshold range is present), the controller 2 executes processing of a step S23.

In the step S23, the controller 2 determines to change a visual aspect of information relevant to the respiration parameter that is outside the threshold range. For example, assume that the value of the respiration rate RR of the patient is 72. In this case, after having determined that the respiration rate RR of the patient is outside the threshold range which is not lower than 40 times/minute and not higher than 60 times/minute, the controller 2 determines to change the visual aspect of the value of the respiration rate RR.

Next, in a step S24, the controller 2 determines to display guide information H in the vicinity of the information relevant to the respiration parameter that is outside the threshold range. For example, in the case where the value of the respiration rate RR is 72, the controller 2 determines to display the guide information H in the vicinity of the value "72" of the respiration rate RR. Details of the guide information H will be given later.

Then, in a step S25, the controller 2 displays the information relevant to the respiration parameters on the display screen 40. Specifically, as shown in FIG. 11, the controller 2 displays, on a display region G10 of the display screen 40, illustration information representing a degree of the leak ratio of the positive pressure ventilation as information about the ventilation volume of the patient. In addition, the controller 2 displays, on a display region G11, the guide information H while displaying, on the display region G11, the value of the respiration rate RR of the patient as the information about the respiration rate of the patient. Further, the controller 2 displays, on a display region G12, the value of the PIP of the patient as information relevant to the PIP of the patient, and displays, on a display region G13, the value of the PEEP of the patient as information relevant to the PEEP of the patient.

In addition, as an example of the visual aspect of the value of the respiration rate RR, the controller 2 may change the display color of the value of the respiration rate RR, as shown in FIG. 11. Specifically, the value "72" of the respiration rate may be displayed on the display region G11 in a state where the display color of the value "72" of the respiration rate RR has been changed from black to white. In addition, as another example of the visual aspect of the value of the respiration rate RR, the value of the respiration rate RR may be displayed on the display region G11 in a state where the value of the respiration rate RR is blinked.

(Guide Information H)

The guide information H will be described in detail below. The guide information H is information which guides the medical worker (user) to perform an operation such that the respiration parameter that is currently outside the threshold range can be included in the threshold range. For example, in the example shown in FIG. 11, the guide information H guides the medical worker to operate the ventilation device 30 so as to make the value of the respiration rate RR be included in the threshold range which is not lower than 40 and not higher than 60. More specifically, since the value "72" of the respiration rate RR is larger than the threshold range, the guide information H guides the medical worker to operate the ventilation device 30 so as to reduce the respiration rate RR.

As shown in FIG. 11, the guide information H may be displayed as graphic information (an animation) which changes continuously with passage of time. In this respect, in the case where the guide information H guides the medical worker so as to reduce the value of the respiration rate RR, the guide information H may be displayed as an animation representing a downward direction. When the guide information H is displayed as the animation, the medical worker can immediately notice the presence of the guide information H displayed on the display screen 40.

Moreover, assume that the value of the respiration rate RR is 30. In this case, since the value "30" of the respiration rate RR is smaller than the threshold range, the guide information H is information which guides the medical worker to operate the ventilation device 30 so as to increase the respiration rate RR. In such a case, the guide information H may be displayed as an animation representing an upward direction in order to increase the value of the respiration rate RR.

In addition, the controller 2 may change the visual aspect of the guide information H in accordance with a difference between the respiration parameter and a predetermined value included in the threshold range of the respiration parameter. For example, the controller 2 may change the visual aspect of the guide information H in accordance with the size of a difference $\Delta RR$ ($=|\beta-\alpha|$) between a predetermined value $\alpha$ (e.g. $\alpha=50$) present in the threshold range ($40 \leq RRth \leq 60$) of the respiration rate RR and a value $\beta$ of the current respiration rate RR. Further, in the case where the guide information H is displayed as an animation, the controller 2 may change display speed of the animation in accordance with the size of the difference $\Delta RR$. For example, the controller 2 may reduce the display speed of the animation in a case where the difference $\Delta RR$ is small. On the other hand, the controller 2 may increase the display speed of the animation in a case where the difference $\Delta RR$ is large.

In addition, in a case where the guide information H is displayed as a still image, the guide information H may be displayed as the still image (e.g. an illustration of an arrow) representing an upward direction or a downward direction. In this case, the controller 2 may change the display color of the guide information H in accordance with the size of the difference $\Delta RR$. For example, the guide information H may be displayed in a first display color in the case where the difference $\Delta RR$ is small. On the other hand, the guide information H may be displayed in a second display color in the case where the difference $\Delta RR$ is large.

On the other hand, in a case where the determination result of the step S22 is NO (in other words, when the respiration parameter that is outside the threshold range is absent), the controller 2 displays the information relevant to the plurality of respiration parameters on the display screen 40 in a normal state (step S26). In this case, all the respiration parameters are displayed in one and the same display color such as black, and the guide information H is not displayed on the display screen 40. In this manner, a series of processes according to the present embodiment are executed.

According to the present embodiment, by visually recognizing the guide information H displayed on the display screen 40, the medical worker who is operating the ventilation device 30 can intuitively grasp abnormality of the respiratory condition of the patient, and can intuitively grasp a measure in order to normalize the respiratory condition of the patient. In the case where, for example, the guide information H is guiding the medical worker so as to reduce the respiration rate RR, the medical worker can suitably adjust operation of the respiration bag 33 by visually recognizing the guide information H. In this manner, usability of the processing apparatus 1 is improved.

In addition, in a case where the predetermined respiration parameter (e.g. the respiration rate RR) is smaller than the threshold range, the guide information H is displayed as graphic information representing an upward direction, on the display screen 40. Therefore, by visually recognizing the guide information H, the medical worker can intuitively grasp the necessity of increasing the predetermined respiration parameter. On the other hand, in a case where the predetermined respiration parameter is larger than the threshold range, the guide information H is displayed as graphic information representing a downward direction, on the display screen 40. Therefore, by visually recognizing the guide information H, the medical worker can intuitively grasp the necessity of reducing the predetermined respiration parameter.

In addition, according to the present embodiment, the visual aspect of the guide information H changes in accordance with the difference between the predetermined respiration parameter (e.g. the respiration rate RR) and the predetermined value included in the threshold range of the predetermined respiration parameter. Therefore, by visually recognizing the change of the visual aspect of the guide information H, the medical worker can intuitively grasp the degree of abnormality of the respiratory condition (e.g. the respiration rate RR) of the patient.

Incidentally, in the description of the present embodiment, the guide information H is displayed on the display region G11 in the case where the value of the respiration rate RR is outside the threshold range. In this respect, guide information may be displayed on each of the display regions G10 to G13 of the display screen 40 when the values of all the plurality of respiration parameters are abnormal.

In addition, in the description of the present embodiment, the information relevant to the respiration parameters is displayed on the display screen 40 after the plurality of respiration parameters have been acquired as an example of the physiological parameters representing the physiological condition of the patient. However, the physiological parameters are not limited to the respiration parameters.

For example, information relevant to a predetermined physiological parameter (such as an ECG parameter or a pulse wave parameter) other than the respiration parameters may be displayed on the display screen 40 after the predetermined physiological parameter has been acquired. In this case, when the predetermined physiological parameter is outside a threshold range, guide information guiding the medical worker to make the predetermined physiological parameter be included in the threshold range may be displayed on the display screen 40.

In addition, the physiological information processing program may be incorporated into the storage device 3 or the ROM in advance in order to realize the processing apparatus 1 according to each of the first embodiment and the second embodiment by software. Alternatively, the physiological information processing program may be stored in a computer-readable storage medium such as a magnetic disk (e.g. an HDD or a floppy disk), an optical disk (e.g. a CD-ROM, a DVD-ROM, or a Blu-ray (registered trademark) disk), a magneto-optical disk (e.g. an MO), or a flash memory (e.g. an SD card, a USB memory, or an SSD). In this case, the physiological information processing program stored in the storage medium may be incorporated into the storage device 3. Further, after the program incorporated into the storage device 3 has been loaded onto the RAM, the processor may execute the program loaded onto the RAM. In this manner, the physiological information processing method according to the present embodiment can be executed by the processing apparatus 1.

In addition, the physiological information processing program may be downloaded through the network interface 4 from a computer on the communication network such as the Internet. Also in this case, the downloaded physiological information processing program may be incorporated into the storage device 3 in a similar manner or the same manner.

Although the embodiment of the present invention has been described above, the technical scope of the present invention should not be interpreted limitedly to the description of the present embodiment. It should be understood by those skilled in the art that the present embodiment is merely an example and various changes can be made on the embodiment within the scope of the invention described in CLAIMS. The technical scope of the present invention should be determined based on the scope of the invention described in CLAIMS and the scope of equivalents thereto.

This application is based on Japanese Patent Application No. 2019-187881 filed on Oct. 11, 2019, the entire contents of which are incorporated herein by reference.

The invention claimed is:

1. A physiological information processing apparatus comprising:

a processor; and a memory that stores a computer-readable instruction that when executed by the processor, causes the physiological information processing apparatus to perform operations comprising:

displaying on a display unit, first attachment position information representing a position where a user is to attach a first physiological information sensor to a subject;

acquiring first physiological information data of the subject from the first physiological information sensor; and displaying, on the display unit, information relevant to the first physiological information data, wherein the physiological information processing apparatus displays the first attachment position information on the display unit before displaying the information relevant to the first physiological information data on the display unit.

2. The physiological information processing apparatus according to claim 1, wherein:

when the physiological information processing apparatus has acquired the first physiological information data, the physiological information processing apparatus changes information displayed on the display unit from the first attachment position information to the information relevant to the first physiological information data.

3. The physiological information processing apparatus according to claim 1, wherein:

when executed by the processor, the computer-readable instruction causes the physiological information processing apparatus to further perform operations comprising:

displaying, on the display unit, second attachment position information representing a position where the user is to attach a second physiological information sensor to the subject;

acquiring second physiological information data of the subject from the second physiological information sensor; and displaying, on the display unit, information relevant to the second physiological information data, the physiological information processing apparatus displays the second attachment position information on the display unit before displaying the information relevant to the second physiological information data on the display unit, and the physiological information processing apparatus simultaneously displays the first attachment position information and the second attachment position information on the display unit.

4. The physiological information processing apparatus according to claim 3, wherein the physiological information processing apparatus:

displays the first attachment position information on a first display region of a display screen of the display unit;

displays the second attachment position information on a second display region of the display screen which is different from the first display region;

displays the information relevant to the first physiological information data on the first display region; and displays the information relevant to the second physiological information data on the second display region.

5. The physiological information processing apparatus according to claim 1, wherein the information relevant to the first physiological information data includes at least one of: a first physiological information waveform representing temporal change of a first parameter representing a vital sign of the subject that has been acquired based on the first physiological information data; and a measurement value of the first parameter.

6. The physiological information processing apparatus according to claim 1, wherein:

when executed by the processor, the computer-readable instruction causes the physiological information processing apparatus to further perform operations comprising:

displaying, on the display unit, second attachment position information representing a position where the user is to attach a second physiological information sensor to the subject; and displaying, on the display unit, third attachment position information representing a position where the user is to attach a third physiological information sensor to the subject, and the physiological information processing apparatus simultaneously displays, on the display unit, the first attachment position information, the second attachment position information, and the third attachment position information.

7. The physiological information processing apparatus according to claim 1, wherein:

the first physiological information sensor is an ECG sensor, the first physiological information data is ECG data, and the information relevant to the first physiological information data is a value of a heart rate identified based on the ECG data.

8. The physiological information processing apparatus according to claim 3, wherein:

the second physiological information sensor is a pulse wave sensor, the second physiological information data is pulse wave data, and the information relevant to the second physiological information data is a value of SpO2 identified based on the pulse wave data.

9. A physiological information processing method executed by a computer, the method comprising:

displaying, on a display unit, first attachment position information representing a position where a user is to attach a first physiological information sensor to a subject;

acquiring first physiological information data of the subject from the first physiological information sensor; and displaying, on the display unit, information relevant to the first physiological information data, wherein the first attachment position information is displayed on the display unit before the information relevant to the first physiological information data is displayed on the display unit.

10. A non-transitory computer-readable recording medium storing a program for causing a computer to perform the physiological information processing method according to claim 9.

* * * * *